US011662453B2

(12) United States Patent
Yu et al.

(10) Patent No.: US 11,662,453 B2
(45) Date of Patent: May 30, 2023

(54) SELF-INJECTION-LOCKED RADAR WITH DIGITAL DEMODULATOR

(71) Applicant: NATIONAL SUN YAT-SEN UNIVERSITY, Kaohsiung (TW)

(72) Inventors: Shiang-Hwua Yu, Kaohsiung (TW); Tzyy-Sheng Horng, Kaohsiung (TW); Wei-Chih Su, Kaohsiung (TW)

(73) Assignee: NATIONAL SUN YAT-SEN UNIVERSITY, Kaohsiung (TW)

( * ) Notice: Subject to any disclaimer, the term of this patent is extended or adjusted under 35 U.S.C. 154(b) by 344 days.

(21) Appl. No.: 17/092,920

(22) Filed: Nov. 9, 2020

(65) Prior Publication Data
US 2021/0341595 A1    Nov. 4, 2021

(30) Foreign Application Priority Data

Apr. 29, 2020   (TW) .................................. 109114331

(51) Int. Cl.
*G01S 7/35*    (2006.01)
*G01S 13/86*   (2006.01)
(Continued)

(52) U.S. Cl.
CPC ............ *G01S 13/536* (2013.01); *G01S 7/352* (2013.01); *G01S 7/354* (2013.01); *G01S 13/862* (2013.01); *A61B 5/0205* (2013.01); *G01S 13/88* (2013.01)

(58) Field of Classification Search
CPC ........ G01S 13/825; G01S 7/352; G01S 7/354; G01S 13/536; G01S 13/862; G01S 13/88; (Continued)

(56) References Cited

U.S. PATENT DOCUMENTS

2017/0353189 A1\*  12/2017  Chen ......................... H03L 7/06
2018/0241406 A1\*   8/2018  Cherniak ................ H03L 7/093
(Continued)

FOREIGN PATENT DOCUMENTS

| TW | 201143312 A1 | 12/2011 |
| TW | 201830048 A  |  8/2018 |
| TW | 202002893 A  |  1/2020 |

OTHER PUBLICATIONS

Shiang-Hwua Yu et al., Highly Linear Phase-Canceling Self-Injection-Locked Ultrasonic Radar for Non-contact Monitoring of Respiration and Heartbeat, IEEE Transactions on Biomedical Circuits and Systems, Dec. 9, 2019.

(Continued)

*Primary Examiner* — Donald HB Braswell
(74) *Attorney, Agent, or Firm* — Demian K Jackson; Jackson IPG PLLC

(57) ABSTRACT

A digital self-injection-locked (SIL) radar includes a digital SIL oscillator, a wireless signal transceiver and a digital frequency demodulator. The digital SIL oscillator generates a digital output signal. The wireless signal transceiver is electrically connected to the digital SIL oscillator to convert the digital output signal into a wireless signal for transmission to a target, receives a reflected signal from the target, and converts the reflected signal into a digital injection signal for injection into the digital SIL oscillator. Accordingly, the digital SIL oscillator operates in an SIL state and generates a digital oscillation signal. The digital frequency demodulator is electrically connected to the digital SIL oscillator to receive and demodulate the digital oscillation signal into a digital demodulation signal.

10 Claims, 6 Drawing Sheets

(51) Int. Cl.
  *G01S 13/536* (2006.01)
  *A61B 5/0205* (2006.01)
  *G01S 13/88* (2006.01)

(58) Field of Classification Search
  CPC ..... G01S 7/415; A61B 5/0205; A61B 5/0245; A61B 5/024; A61B 5/0507; A61B 5/1135; A61B 5/7203
  See application file for complete search history.

(56) References Cited

U.S. PATENT DOCUMENTS

| | | | |
|---|---|---|---|
| 2019/0131982 A1* | 5/2019 | Hsiao | ............ H02M 3/07 |
| 2019/0175117 A1 | 6/2019 | Tseng et al. | |
| 2020/0106387 A1* | 4/2020 | Bassi | ............ H03B 5/1215 |

OTHER PUBLICATIONS

Taiwanese Office Action dated Sep. 23, 2020 for Taiwanese Patent Application No. 109114331, 7 pages.
Taiwanese Notice of Allowance dated Oct. 14, 2020 for Taiwanese Patent Application No. 109114331, 3 pages.

* cited by examiner

SELF-INJECTION-LOCKED RADAR WITH DIGITAL DEMODULATOR

FIELD OF THE INVENTION

This invention generally relates to a self-injection-locked (SIL) radar, and more particularly to a digital SIL radar.

BACKGROUND OF THE INVENTION

SIL radar is a continuous-wave (CW) radar with low complexity and high sensitivity and suitable for monitoring vital signs without contact. In an SIL radar, due to the Doppler effect induced by relative motion between a target and a transmit antenna, an echo signal containing the Doppler phase shift is reflected from the target and received by a receive antenna for injection into an oscillator. By doing so, the oscillator enters an SIL state and outputs a frequency-modulated signal. The movement of the target can be detected by demodulating the frequency-modulated signal with a frequency demodulator at the output of the oscillator. The target's tiny movements due to vital signs, such as respiration and heartbeat, can be successfully measured by the SIL radar because of high sensitivity. However, the sensitivity of the SIL radar is vulnerable to the noise injected into the oscillator and the distortion of the frequency demodulator. These are the main reasons to cause degradation of the performance of the SIL radar.

SUMMARY

The digital SIL radar of the present invention is programmable with high flexibility. Additionally, it can effectively resolve the noise and distortion problems in conventional SIL radars.

One aspect of the present invention provides a digital SIL radar that includes a digital SIL oscillator, a wireless signal transceiver and a digital frequency demodulator. A digital output signal from the digital SIL oscillator is converted and transmitted to a target as a wireless signal by the wireless signal transceiver that is electrically connected to the digital SIL oscillator. A reflected signal from the target is received by the wireless signal transceiver and then converted into a digital injection signal for injection into the digital SIL oscillator. The digital SIL oscillator under injection operates in an SIL state and generates a digital oscillation signal. The digital oscillation signal is received and demodulated by the digital frequency demodulator that is electrically connected to the digital SIL oscillator to obtain a digital demodulation signal for detecting vital signs of the target.

The digital SIL radar of the present invention has high programming capability and design flexibility due to digitalization. Moreover, it is highly sensitive and linear in the detection of the target's vital signs because of low noise and distortion.

DETAILED DESCRIPTION OF THE INVENTION

Figure 1:
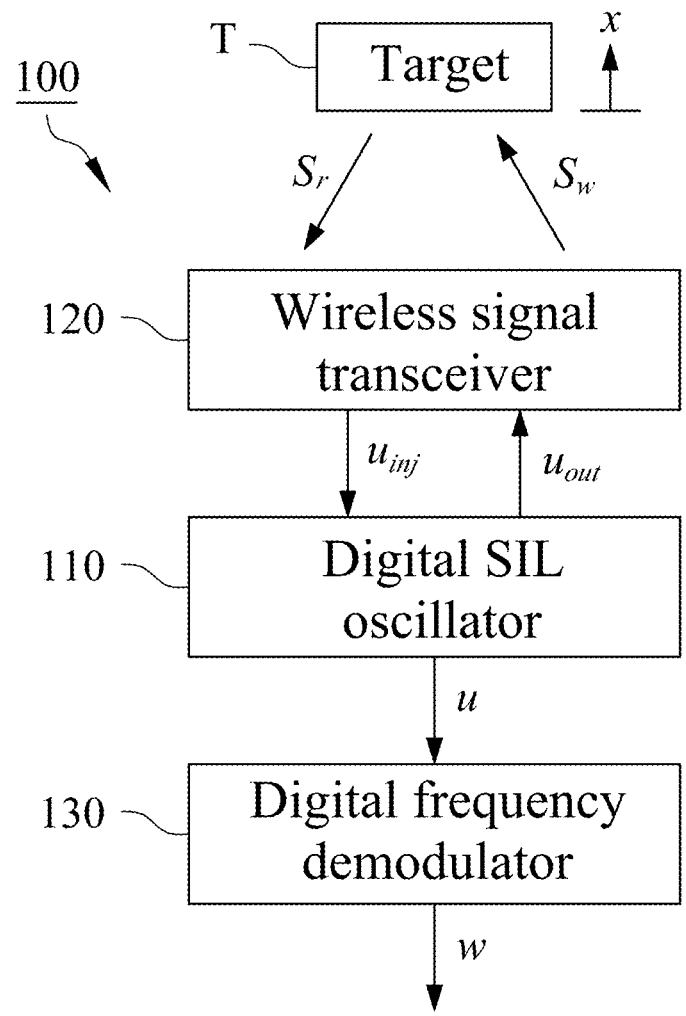
FIG. 1 is a block diagram illustrating a digital SIL radar in accordance with one embodiment of the present invention.

FIG. 1 is a block diagram showing a digital SIL radar 100 in accordance with an embodiment of the present invention. The digital SIL radar 100 includes a digital SIL oscillator 110, a wireless signal transceiver 120 and a digital frequency demodulator 130. The digital SIL oscillator 110 generates a digital output signal $u_{out}$. The wireless signal transceiver 120 is electrically connected to the digital SIL oscillator 110 to convert the digital output signal $u_{out}$ into a wireless signal $S_w$ for transmission to a target T, and receive a reflected signal $S_r$ from the target T. The wireless signal $S_w$ and the reflected signal $S_r$ are electromagnetic or ultrasonic signals. The wireless signal transceiver 120 converts the reflected signal $S_r$ into a digital injection signal $u_{inj}$ for injection into the digital SIL oscillator 110. Accordingly, the digital SIL oscillator 110 operates in an SIL state and generates a digital oscillation signal u.

While a displacement x of the target T relative to the wireless signal transceiver 120 happens, the digital injection signal $u_{inj}$ of the digital SIL oscillator 110 has a Doppler phase shift as a result of the Doppler effect on the reflected signal $S_r$. Under the SIL condition, the digital oscillation signal u is frequency-modulated with the Doppler phase shift of the digital injection signal $u_{inj}$. The digital frequency demodulator 130 is electrically connected to the digital SIL oscillator 110 to demodulate the digital oscillation signal u into a digital demodulation signal w that contains the information of the displacement x.

Figure 2:
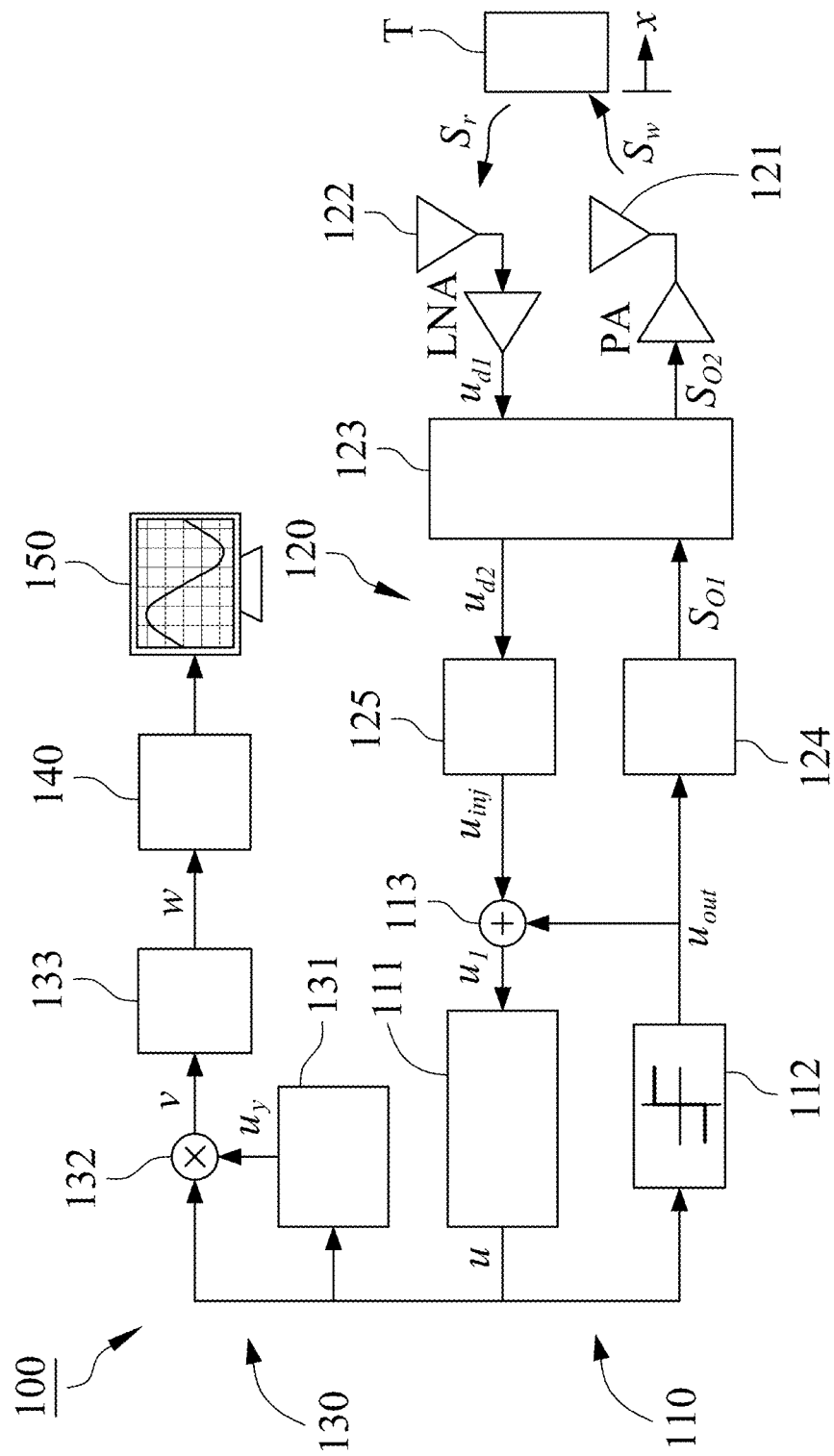
FIG. 2 is a circuit diagram illustrating an SIL radar in accordance with a first embodiment of the present invention.

A digital SIL radar 100 of a first embodiment of the present invention is shown in FIG. 2. The digital SIL oscillator 110 of the first embodiment includes a digital resonator 111, a digital comparator 112 and a first digital adder 113. The digital resonator 111 outputs the digital oscillation signal u. The digital comparator 112 is electrically connected to the digital resonator 111 to compare the digital oscillation signal u with a digital threshold level and thus outputs the digital output signal $u_{out}$. The digital comparator 112 is used as a digital amplifier to sustain the oscillation of the digital resonator 111. The first digital adder 113 is electrically connected to the digital comparator 112 and the wireless signal transceiver 120 for adding the digital output signal $u_{out}$ and the digital injection signal $u_{inj}$ to produce a digital added signal $u_1$ for inputting to the digital resonator 111. Preferably, the digital resonator 111, the digital comparator 112 and the first digital adder 113 are integrated in a field programmable gate array (FPGA) or an application-specific integrated circuit (ASIC). As a result of doing so, the digital SIL oscillator 110 features good noise immunity.

As shown in FIG. 2, the wireless signal transceiver 120 of the first embodiment includes a transmit antenna 121, a receive antenna 122, an image rejection frequency converter 123, a first digital-to-analog converter (DAC) 124 and an analog-to-digital converter (ADC) 125. The first DAC 124 is electrically connected to the digital comparator 112 to convert the digital output signal $u_{out}$ into a low-frequency analog output signal $S_{O1}$. The image rejection frequency converter 123 is electrically connected to the first DAC 124 to up-convert the low-frequency analog output signal $S_{O1}$ into a high-frequency analog output signal $S_{O2}$.

The transmit antenna 121 is coupled to the image rejection frequency converter 123 via a power amplifier PA to transmit the power-amplified high-frequency analog output signal $S_{O2}$ to the target T as the wireless signal $S_w$. The receive antenna 122 receives the reflected signal $S_r$ from the target T as a high-frequency analog detection signal $u_{d1}$. The image rejection frequency converter 123 is coupled to the receive antenna 122 via a low noise amplifier LNA to down-convert the low-noise-amplified high-frequency analog detection signal $u_{d1}$ into a low-frequency analog detection signal $u_{d2}$ in which the image signal has been eliminated. The ADC 125 is electrically connected to the image rejection frequency converter 123 to convert the low-frequency analog detection signal $u_{d2}$ into the digital injection signal $u_{inj}$. The digital injection signal $u_{inj}$ is delivered to the first digital adder 113 of the digital SIL oscillator 110. The digital injection signal $u_{inj}$ is used as a feedback signal from the output to the input of the digital SIL oscillator 110 to make the digital SIL oscillator 110 operate in the SIL state.

With reference to FIG. 2 again, the digital frequency demodulator 130 includes a digital delay 131, a digital multiplier 132 and a digital low-pass filter 133 in the first embodiment. The digital delay 131 is electrically connected to the digital resonator 111 of the digital SIL oscillator 110 to provide a delay time to the digital oscillation signal u, and thus outputs a digital delayed signal $u_y$. The digital multiplier 132 is electrically connected to the digital resonator 111 and the digital delay 131 to multiply the digital oscillation signal u with the digital delayed signal $u_y$, and thus outputs a digital multiplied signal v. The digital low-pass filter 133 is electrically connected to the digital multiplier 132 to extract the low frequency component of the digital multiplied signal v as a digital demodulation signal w. In the first embodiment, the digital delay 131, the digital multiplier 132 and the digital low-pass filter 133 are also integrated in the FPGA or ASIC to improve the distortion of the digital frequency demodulator 130.

The digital demodulation signal w is converted into an analog demodulation signal by a second DAC 140 that is electrically connected to the digital low-pass filter 133 of the digital frequency demodulator 130. Then, the analog demodulation signal is processed by a computer 150 to obtain the displacement x. Furthermore, when the target T is a biological subject and the displacement x is caused by the vital signs of the biological subject, the vital signs of the target T can be identified in the spectrum of the displacement x. Because of digitization, the digital SIL radar 100 of this embodiment has advantages of high programmability, low noise and low distortion.

Figure 3:
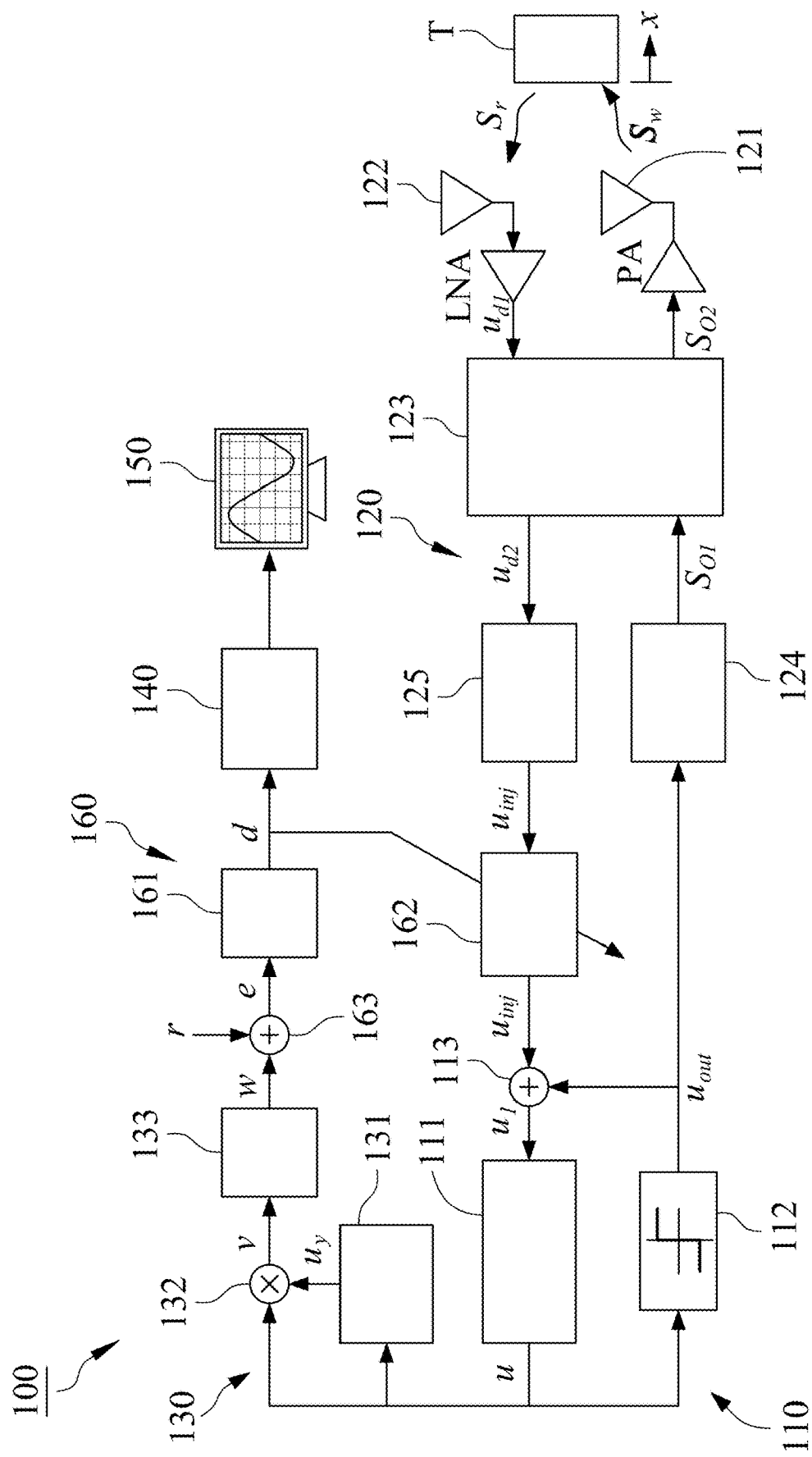
FIG. 3 is a circuit diagram illustrating an SIL radar in accordance with a second embodiment of the present invention.

FIG. 3 is a circuit diagram illustrating a digital SIL radar 100 of a second embodiment that further includes a digital phase regulator 160. The digital phase regulator 160 is electrically connected to the digital frequency demodulator 130, the wireless signal transceiver 120 and the digital SIL oscillator 110. In the second embodiment, the digital phase regulator 160 includes a digital controller 161, a digital adjustable delay 162 and a second digital adder 163. The second digital adder 163 is electrically connected to the digital frequency demodulator 130 to add a set-point digital signal r to the digital demodulation signal w, and thus outputs a digital error signal e. The digital controller 161 is electrically connected to the second digital adder 163 to receive the digital error signal e and produce a digital displacement signal d according to the digital error signal e. In the second embodiment, the set-point digital signal r is used to reduce the frequency shift of the digital SIL oscillator 110.

The digital adjustable delay 162 is electrically connected to the digital controller 161, the wireless signal transceiver 120 and the digital SIL oscillator 110 to adjust the delay time of the digital injection signal $u_{inj}$ output from the wireless signal transceiver 120 according to the digital displacement signal d before injecting the digital injection signal $u_{inj}$ into the digital SIL oscillator 110. The delay adjustment of the digital injection signal $u_{inj}$ is controlled by the digital phase regulator 160 to cancel the Doppler phase shift caused by the displacement x of the target T. Accordingly, the displacement x can be extracted from the analog version of the digital displacement signal d output from the digital phase regulator 160.

In the second embodiment, the displacement x is detected based on a phase-canceling technique. For this reason, the drawbacks of the conventional SIL radar, e.g. nonlinear distortion and null point, are solved. Therefore, the SIL radar 100 can detect the target T with a larger range of movement than the convention SIL radar.

Figure 4:
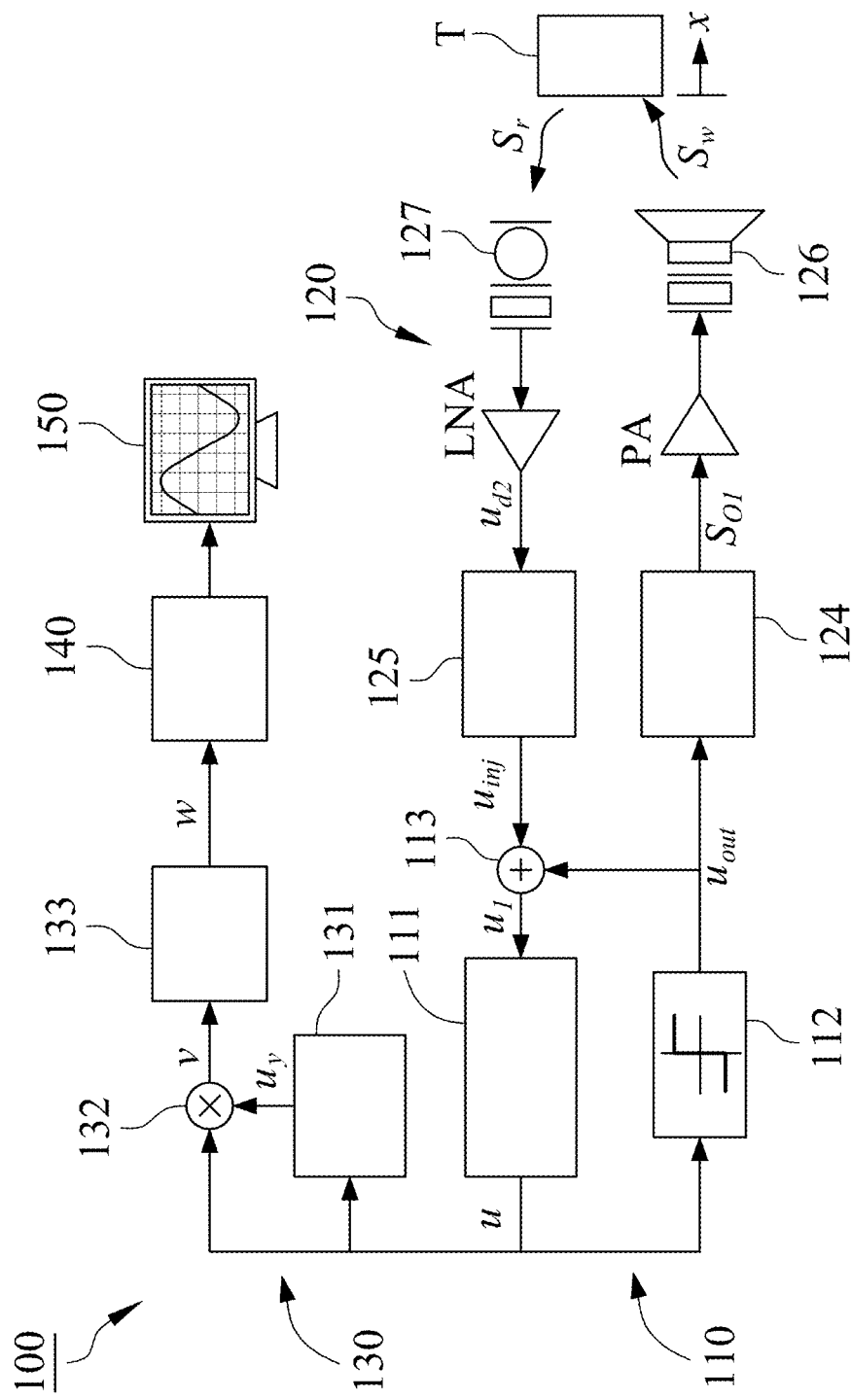
FIG. 4 is a circuit diagram illustrating an SIL radar in accordance with a third embodiment of the present invention.

FIG. 4 shows a digital SIL radar 100 of a third embodiment of the present invention. The transmit antenna 121 and the receive antenna 122 are replaced by an ultrasonic transmitter 126 and an ultrasonic receiver 127 in the wireless signal transceiver 120 of the third embodiment, and the image rejection frequency converter 123 is not used. The ultrasonic transmitter 126 is electrically connected to the first DAC 124 via the power amplifier PA to transmit the power-amplified low-frequency analog output signal $S_{O1}$ as the wireless signal $S_w$. The reflected signal $S_r$ from the target T is received by the ultrasonic receiver 127 and then low-noise-amplified by the low noise amplifier LNA as the low-frequency analog detection signal $u_{d2}$ that is converted into the digital injection signal $u_{inj}$ by the ADC 125. In the third embodiment, the wireless signal $S_w$ and the reflected signal $S_r$ are ultrasonic signals. While the target moves, the digital injection signal $u_{inj}$ of the digital SIL oscillator 110 contains the Doppler phase shift caused by the displacement x of the target T because of the Doppler effect on the reflected signal $S_r$. Under the SIL condition, the digital oscillation signal u is frequency-modulated with the Doppler phase shift of the digital injection signal $u_{inj}$. Then, the digital demodulation signal w is obtained by demodulating the digital oscillation signal u with the digital frequency demodulator 130. Finally, with the help of the second DAC 140 and the computer 150, the displacement x of the target T is extracted from the analog version of the digital demodulation signal w. Moreover, the vital signs of the target T can be identified in the spectrum of the displacement x.

Figure 5:
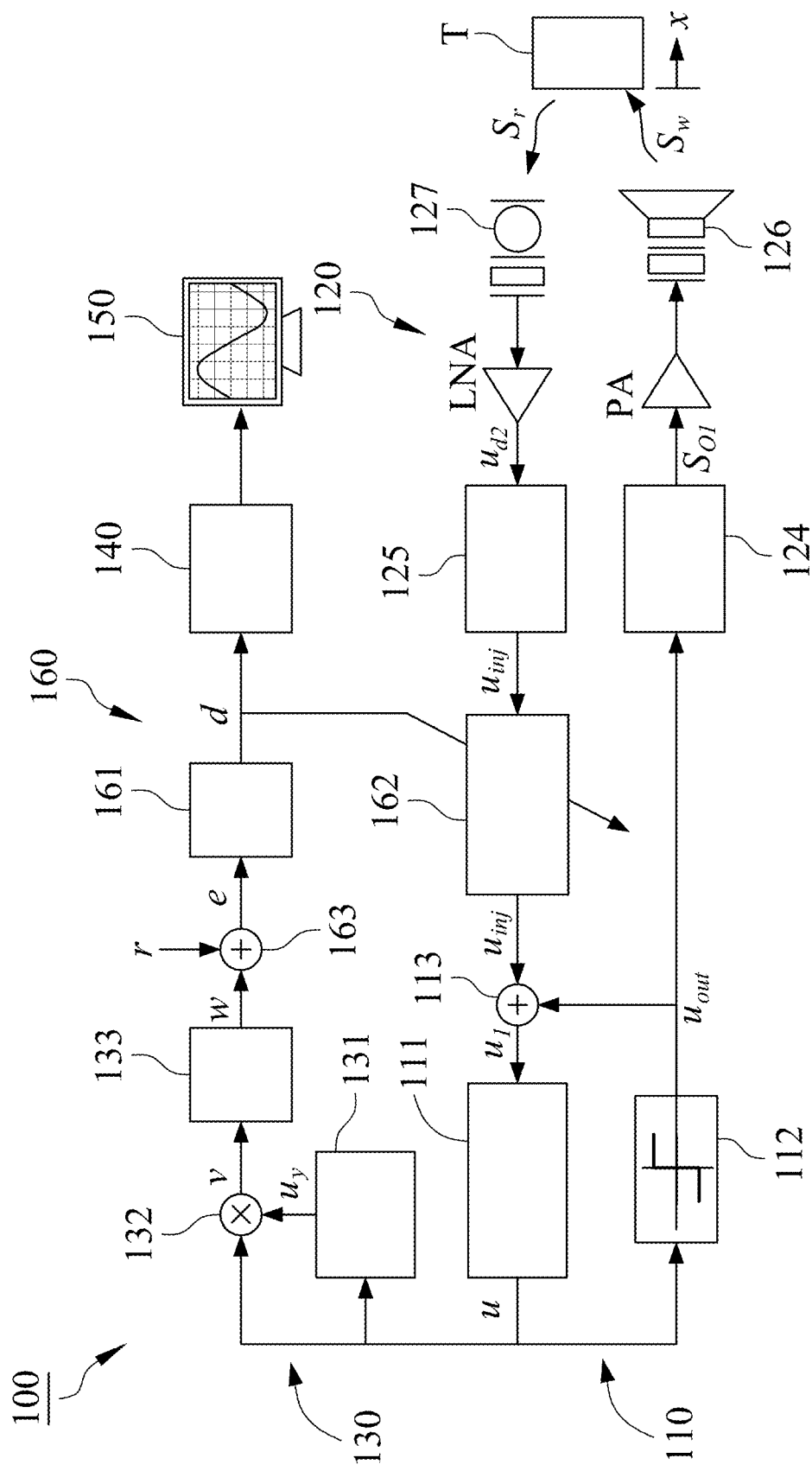
FIG. 5 is a circuit diagram illustrating an SIL radar in accordance with a fourth embodiment of the present invention.

Different from the digital SIL radar 100 of the third embodiment, a digital SIL radar 100 of a fourth embodiment shown in FIG. 5 further includes the digital phase regulator 160 that is electrically connected to the digital frequency demodulator 130, the wireless signal transceiver 120 and the digital SIL oscillator 110. In the fourth embodiment, the digital phase regulator 160 also includes the digital controller 161, the digital adjustable delay 162 and the second digital adder 163. The second digital adder 163 is electrically connected to the digital frequency demodulator 130 to add the set-point digital signal r to the digital demodulation signal w, and thus outputs the digital error signal e. The digital controller 161 is electrically connected to the second digital adder 163 to receive the digital error signal e and produce the digital displacement signal d according to the digital error signal e. The set-point digital signal r is also used to reduce the frequency shift of the digital SIL oscillator 110 in the fourth embodiment.

Since the digital adjustable delay 162 is electrically connected to the digital controller 161, the wireless signal transceiver 120 and the digital SIL oscillator 110, the digital injection signal $u_{inj}$ output from the wireless signal transceiver 120 has a delay time varying with the digital displacement signal d before it is injected into the digital SIL oscillator 110. The digital phase regulator 160 is provided to control the delay time of the digital injection signal $u_{inj}$ to cancel the Doppler phase shift of the digital injection signal $u_{inj}$ caused by the displacement x of the target T. Accordingly, the displacement x can be extracted from the analog version of the digital displacement signal d output from the digital phase regulator 160.

Figure 6:
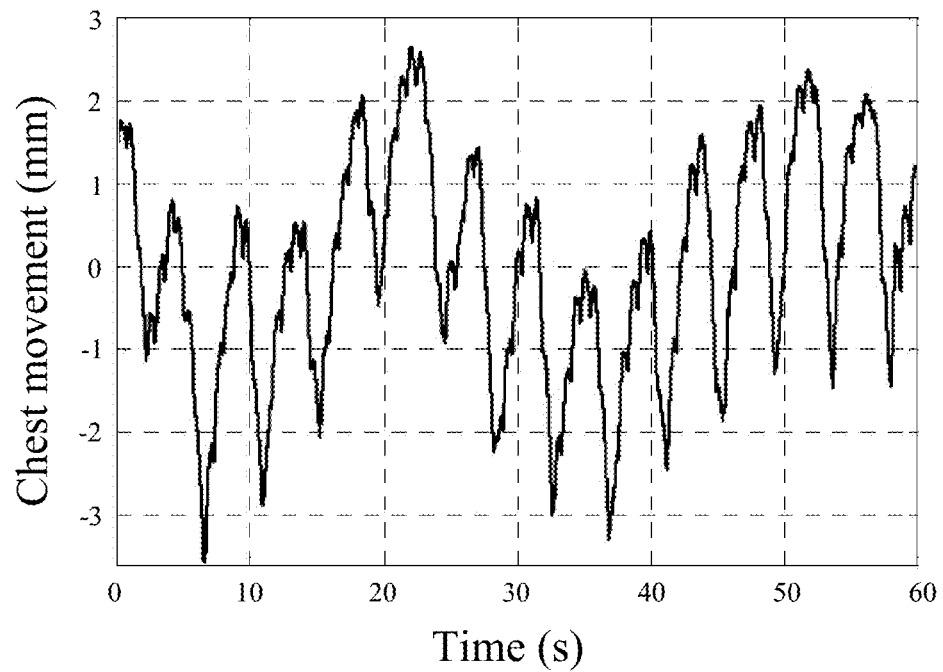
FIG. 6 shows a detection result of human chest movements using the SIL radar in accordance with the fourth embodiment of the present invention.
Figure 7:
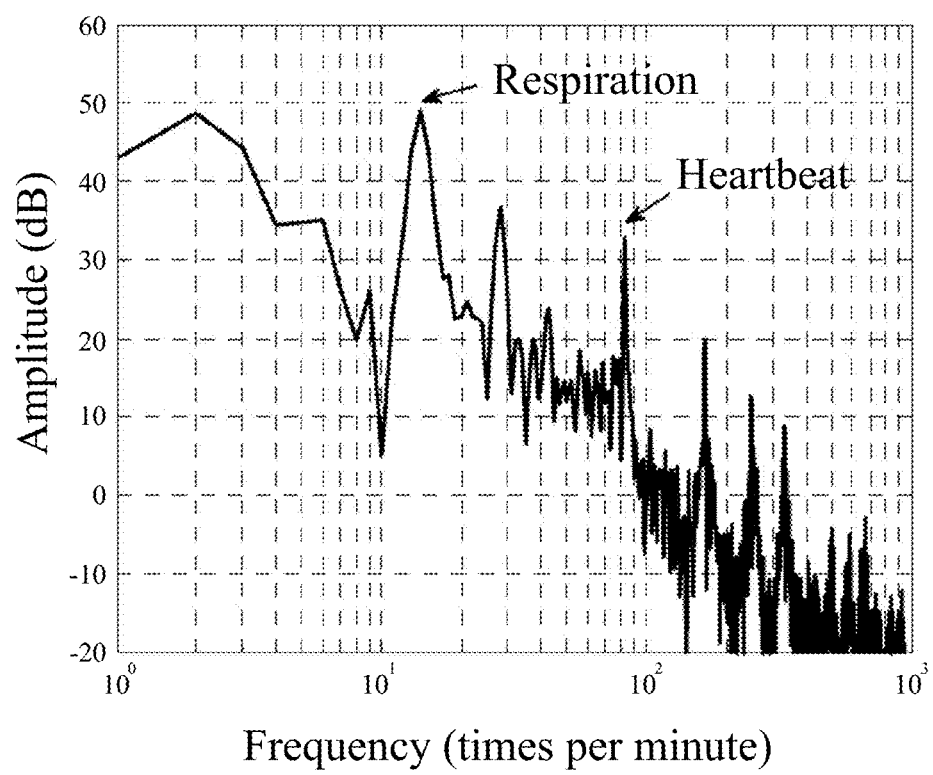
FIG. 7 shows the spectrum of the detection data in FIG. 6.

FIG. 6 shows the result of using the digital SIL radar 100 of the fourth embodiment to detect chest movements of an examinee located at a distance of 30 cm from the radar. The detected result shown in FIG. 6 includes the involuntary body movements and the periodic movements due to vital signs. FIG. 7 is the spectrum of the detection data presented in FIG. 6 where the arrows point at the fundamental respiration and heartbeat signals with the frequencies of 14 times per minute and 83 times per minute, respectively. The detected heart rate of 83 times per minute is very close to the pulse rate of 82.4 times per minute determined from the photoplethysmogram (PPG) measurement. This result demonstrates that the digital SIL radar 100 of the present invention is capable of monitoring vital signs without contact.

While this invention has been particularly illustrated and described in detail with respect to the preferred embodiments thereof, it will be clearly understood by those skilled in the art that is not limited to the specific features shown and described and various modified and changed in form and details may be made without departing from the spirit and scope of this invention.

What is claimed is:

1. A digital self-injection-locked radar comprising:
  a digital self-injection-locked (SIL) oscillator configured to output a digital output signal;
  a wireless signal transceiver electrically connected to the digital SIL oscillator, the wireless signal transceiver is configured to convert the digital output signal into a wireless signal and transmit the wireless signal to a target, the wireless signal transceiver is further configured to receive a reflected signal from the target and convert the reflected signal into a digital injection signal for injection into the digital SIL oscillator to make the digital SIL oscillator operate in an SIL state and generate a digital oscillation signal; and
  a digital frequency demodulator electrically connected to the digital SIL oscillator, the digital frequency demodulator is configured to receive and demodulate the digital oscillation signal into a digital demodulation signal,
  wherein the digital SIL oscillator includes a digital resonator, a digital comparator and a first digital adder, the digital resonator is configured to output the digital oscillation signal, the digital comparator is electrically connected to the digital resonator and configured to receive the digital oscillation signal and output the digital output signal, the first digital adder is electrically connected to the digital comparator and the wireless signal transceiver, the first digital adder is configured to receive the digital output signal and the digital injection signal and configured to output a digital added signal to the digital resonator.

2. The digital self-injection-locked radar in accordance with claim 1, wherein the wireless signal transceiver includes a transmit antenna, a receive antenna, an image rejection frequency converter, a first digital-to-analog converter (DAC) and an analog-to-digital converter (ADC), the first DAC is electrically connected to the digital comparator and configured to receive and convert the digital output signal into a low-frequency analog output signal, the image rejection frequency converter is electrically connected to the first DAC and configured to receive and up-convert the low-frequency analog output signal into a high-frequency analog output signal, the transmit antenna is electrically connected to the image rejection frequency converter and configured to transmit the high-frequency analog output signal to the target as the wireless signal, the receive antenna is configured to receive the reflected signal from the target as a high-frequency analog detection signal, the image rejection frequency converter is electrically connected to the receive antenna and configured to down-convert the high-frequency analog detection signal into a low-frequency analog detection signal, the ADC is electrically connected to the image rejection frequency converter and configured to receive and convert the low-frequency analog detection signal into the digital injection signal.

3. The digital self-injection-locked radar in accordance with claim 1, wherein the digital frequency demodulator includes a digital delay, a digital multiplier and a digital low-pass filter, the digital delay is electrically connected to the digital resonator and configured to receive the digital oscillation signal and output a digital delayed signal, the digital multiplier is electrically connected to the digital resonator and the digital delay, configured to receive the digital oscillation signal and the digital delayed signal and configured to output a digital multiplied signal, the digital low-pass filter is electrically connected to the digital multiplier and configured to receive the digital multiplied signal and output the digital demodulation signal.

4. The digital self-injection-locked radar in accordance with claim 1 further comprising a digital phase regulator, wherein the digital phase regulator includes a digital controller, a digital adjustable delay and a second digital adder, the second digital adder is electrically connected to the digital frequency demodulator and configured to add a set-point digital signal to the digital demodulation signal and output a digital error signal, the set-point digital signal is configured to reduce the frequency shift of the digital SIL oscillator, the digital controller is electrically connected to the second digital adder and configured to receive the digital error signal and output a digital displacement signal according to the digital error signal, the digital adjustable delay is electrically connected to the digital controller, the wireless signal transceiver and the digital SIL oscillator, configured to adjust a delay time of the digital injection signal output from the wireless signal transceiver according to the digital displacement signal before injecting the digital injection signal into the digital SIL oscillator.

5. The digital self-injection-locked radar in accordance with claim 1, wherein the wireless signal transceiver includes an ultrasonic transmitter, an ultrasonic receiver, a first digital-to-analog converter (DAC) and an analog-to-digital converter (ADC), the first DAC is electrically connected to the digital comparator and configured to receive and convert the digital output signal into an analog output signal, the ultrasonic transmitter is electrically connected to the first DAC and configured to receive and transmit the analog output signal as the wireless signal, the ultrasonic receiver is configured to receive the reflected signal as an analog detection signal, the ADC is electrically connected to the ultrasonic receiver and configured to receive and convert the analog detection signal into the digital injection signal.

6. The digital self-injection-locked radar in accordance with claim 1 further comprising a second digital-to-analog converter (DAC) and a computer, wherein the second DAC is electrically connected to the digital frequency demodulator and configured to receive and convert the digital demodulation signal into an analog demodulation signal, the computer is electrically connected to the second DAC and configured to receive the analog demodulation signal and extract a displacement of the target from the analog demodulation signal.

7. The digital self-injection-locked radar in accordance with claim 4 further comprising a second digital-to-analog converter (DAC) and a computer, wherein the second DAC is electrically connected to the digital controller of the digital phase regulator and configured to receive and convert the digital displacement signal into an analog displacement signal, the computer is electrically connected to the second DAC and configured to receive the analog displacement signal and extract a displacement of the target from the analog displacement signal.

8. A digital self-injection-locked radar comprising:
   a digital self-injection-locked (SIL) oscillator configured to output a digital output signal;
   a wireless signal transceiver electrically connected to the digital SIL oscillator, the wireless signal transceiver is configured to convert the digital output signal into a wireless signal and transmit the wireless signal to a target, the wireless signal transceiver is further configured to receive a reflected signal from the target and convert the reflected signal into a digital injection signal for injection into the digital SIL oscillator to make the digital SIL oscillator operate in an SIL state and generate a digital oscillation signal;
   a digital frequency demodulator electrically connected to the digital SIL oscillator, the digital frequency demodulator is configured to receive and demodulate the digital oscillation signal into a digital demodulation signal; and
   a digital phase regulator, wherein the digital phase regulator includes a digital controller, a digital adjustable delay and a second digital adder, the second digital adder is electrically connected to the digital frequency demodulator and configured to add a set-point digital signal to the digital demodulation signal and output a digital error signal, the set-point digital signal is configured to reduce the frequency shift of the digital SIL oscillator, the digital controller is electrically connected to the second digital adder and configured to receive the digital error signal and output a digital displacement signal according to the digital error signal, the digital adjustable delay is electrically connected to the digital controller, the wireless signal transceiver and the digital SIL oscillator, configured to adjust a delay time of the digital injection signal output from the wireless signal transceiver according to the digital displacement signal before injecting the digital injection signal into the digital SIL oscillator.

9. The digital self-injection-locked radar in accordance with claim 8 further comprising a second digital-to-analog converter (DAC) and a computer, wherein the second DAC is electrically connected to the digital controller of the digital phase regulator and configured to receive and convert the digital displacement signal into an analog displacement signal, the computer is electrically connected to the second DAC and configured to receive the analog displacement signal and extract a displacement of the target from the analog displacement signal.

10. A digital self-injection-locked radar comprising:
    a digital self-injection-locked (SIL) oscillator configured to output a digital output signal;
    a wireless signal transceiver electrically connected to the digital SIL oscillator, the wireless signal transceiver is configured to convert the digital output signal into a wireless signal and transmit the wireless signal to a target, the wireless signal transceiver is further configured to receive a reflected signal from the target and convert the reflected signal into a digital injection signal for injection into the digital SIL oscillator to make the digital SIL oscillator operate in an SIL state and generate a digital oscillation signal;
    a digital frequency demodulator electrically connected to the digital SIL oscillator, the digital frequency demodulator is configured to receive and demodulate the digital oscillation signal into a digital demodulation signal; and
    a second digital-to-analog converter (DAC) and a computer, wherein the second DAC is electrically connected to the digital frequency demodulator and configured to receive and convert the digital demodulation signal into an analog demodulation signal, the computer is electrically connected to the second DAC and configured to receive the analog demodulation signal and extract a displacement of the target from the analog demodulation signal.

* * * * *